US008911265B2

(12) United States Patent
Maio et al.

(10) Patent No.: US 8,911,265 B2
(45) Date of Patent: Dec. 16, 2014

(54) ELECTRICAL CONNECTION PLUG FOR MULTIPOLAR LEAD OF ACTIVE IMPLANTABLE MEDICAL DEVICE

(71) Applicant: Sorin CRM SAS, Clamart (FR)

(72) Inventors: Luciano Di Maio, Turin (IT); Mylène Roussin, Mazzè (IT); Hélène Viatgé, Montrouge (FR)

(73) Assignee: Sorin CRM SAS, Clamart (FR)

( * ) Notice: Subject to any disclaimer, the term of this patent is extended or adjusted under 35 U.S.C. 154(b) by 29 days.

(21) Appl. No.: 13/857,033

(22) Filed: Apr. 4, 2013

(65) Prior Publication Data

US 2013/0267127 A1 Oct. 10, 2013

(30) Foreign Application Priority Data

Apr. 4, 2012 (FR) ...................... 12 53103

(51) Int. Cl.
*H01R 13/64* (2006.01)
*A61N 1/375* (2006.01)
*H01R 24/58* (2011.01)
*H01R 13/58* (2006.01)
*H01R 43/26* (2006.01)
*H01R 13/41* (2006.01)
*H01R 105/00* (2006.01)
*H01R 13/502* (2006.01)

(52) U.S. Cl.
CPC ............ *H01R 13/58* (2013.01); *H01R 2105/00* (2013.01); *A61N 1/3752* (2013.01); *H01R 24/58* (2013.01); *H01R 43/26* (2013.01); *H01R 13/41* (2013.01); *H01R 13/502* (2013.01)
USPC ......................................... 439/699

(58) Field of Classification Search
CPC ................................ H01R 13/26; H01R 33/09
USPC ................ 439/669, 668, 909, 191, 190, 199; 607/72
See application file for complete search history.

(56) References Cited

U.S. PATENT DOCUMENTS 4,898,173 A * 2/1990 Daglow et al. .................. 607/37
6,248,080 B1 6/2001 Miesel et al.
(Continued)

FOREIGN PATENT DOCUMENTS

FR 1 641 084 3/2006

OTHER PUBLICATIONS

Preliminary Search Report for French Patent Application No. 1253103, dated Sep. 6, 2012, 2 pages.

*Primary Examiner* — Phuongchi T Nguyen
(74) *Attorney, Agent, or Firm* — Foley & Lardner LLP

(57) ABSTRACT

A plug includes a pin having an axial contact at its opposite end with a mounting rod connected to a center conductor. At the interface between the pin and the inner wall of the plug body, a support sleeve mounted on the shaft and bearing axially against a collar formed on said rod is provided. Axially, a locking ring is secured to the shaft so that the support sleeve is clamped between the collar of the rod and the locking ring, if necessary, leaving a degree of freedom of rotation between the sleeve and the pin. Radially, the outer surface of the sleeve comes into direct contact with the inner wall of the bore of the plug body, to which it is directly secured. The direct attachment of the sleeve to the plug body may be obtained by a snap-in connection with notches cooperating with a counterpart groove.

17 Claims, 6 Drawing Sheets

(56) References Cited

U.S. PATENT DOCUMENTS

| | | |
|---|---|---|
| 7,241,180 B1 | 7/2007 | Rentas Torres |
| 8,382,529 B2 * | 2/2013 | Lim et al. .................... 439/669 |
| 8,556,664 B2 * | 10/2013 | Aase .............................. 439/668 |
| 8,577,463 B2 * | 11/2013 | Arnholt et al. ................... 607/37 |
| 8,602,827 B2 * | 12/2013 | Lim et al. ...................... 439/669 |
| 2006/0068645 A1 | 3/2006 | Ollivier |
| 2010/0211144 A1 | 8/2010 | Jang et al. |
| 2011/0144722 A1 | 6/2011 | Min et al. |

* cited by examiner

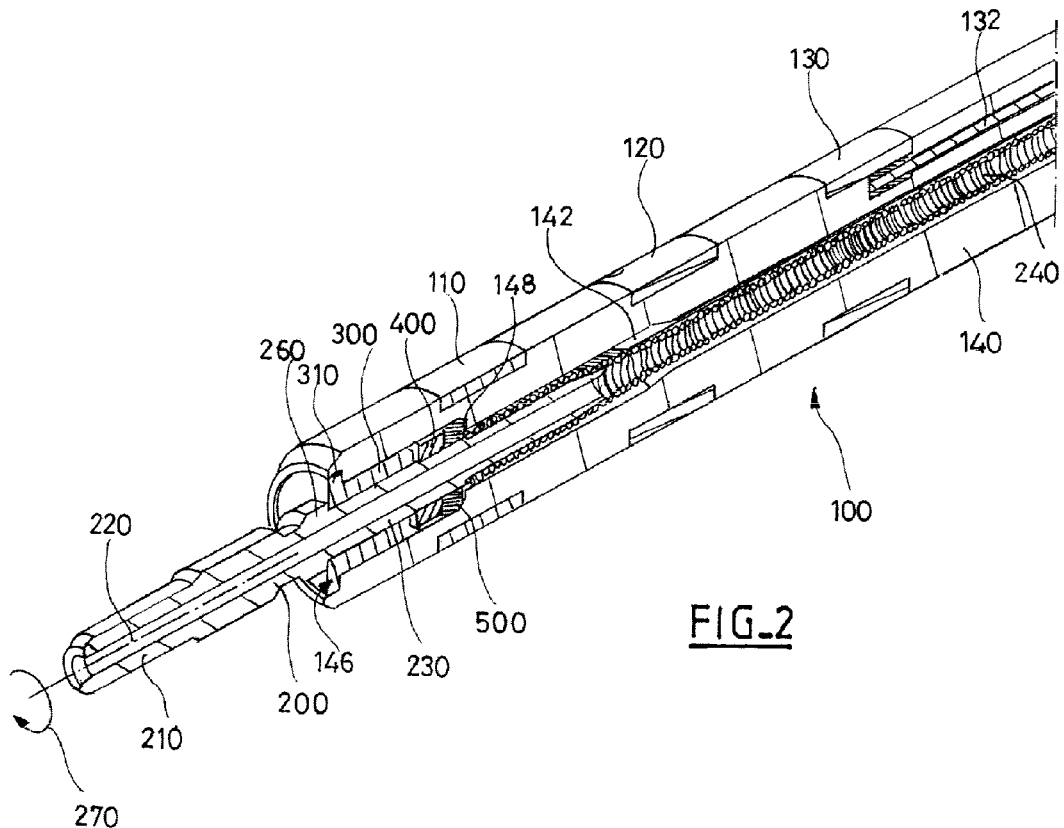
FIG_2
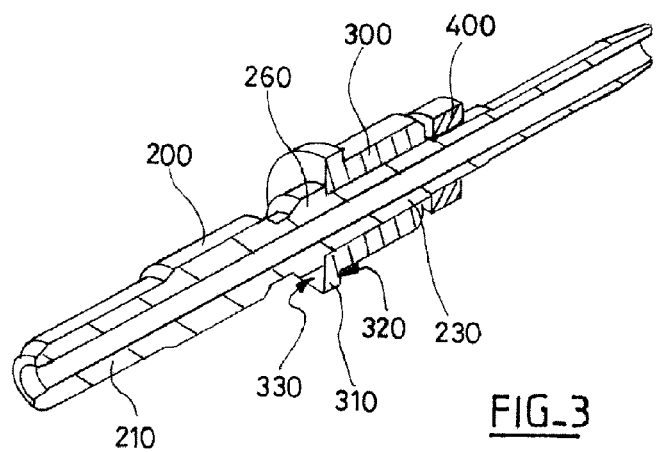
FIG_3

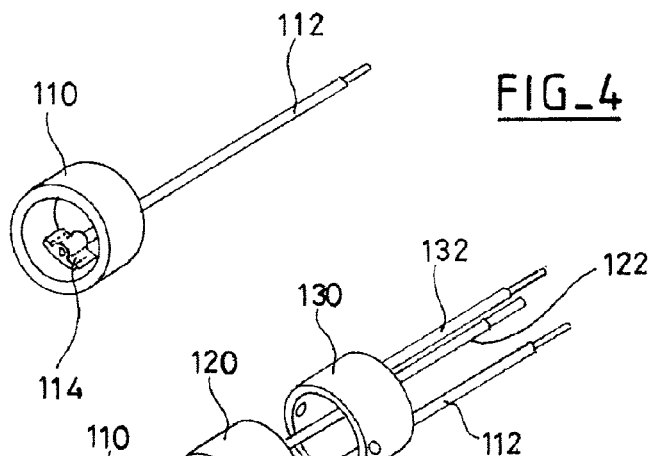
FIG_4
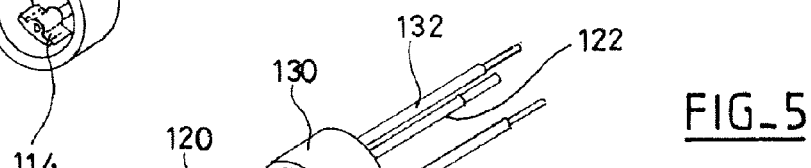
FIG_5
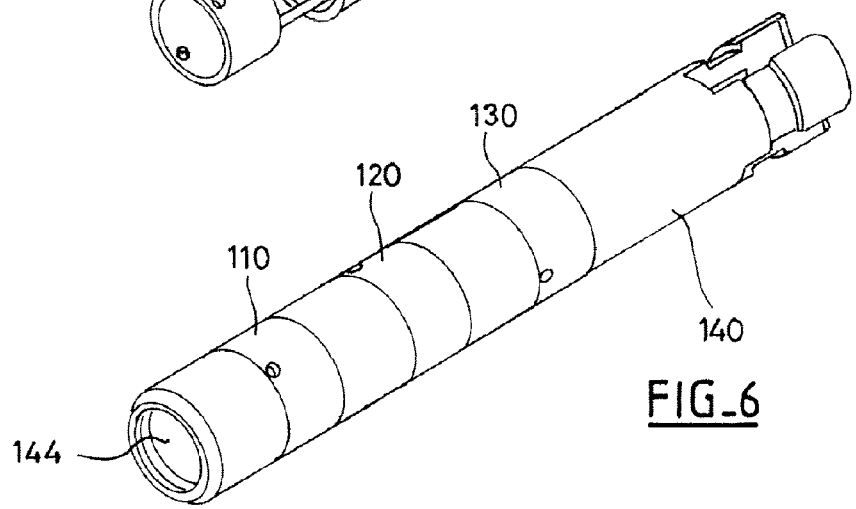
FIG_6
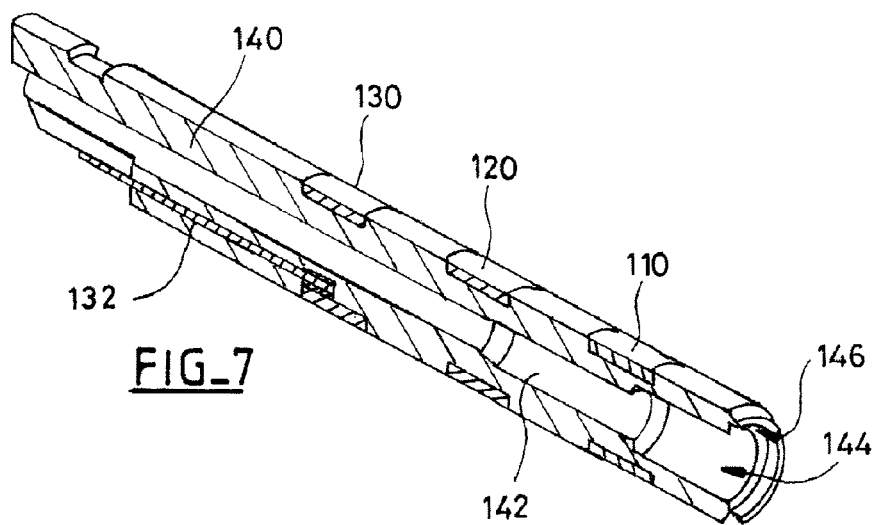
FIG_7

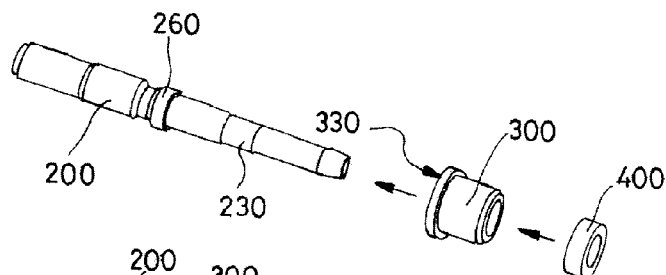
FIG_8
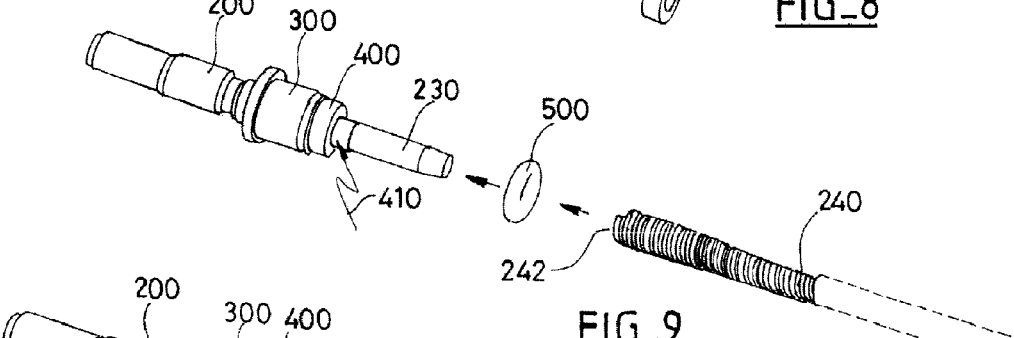
FIG_9
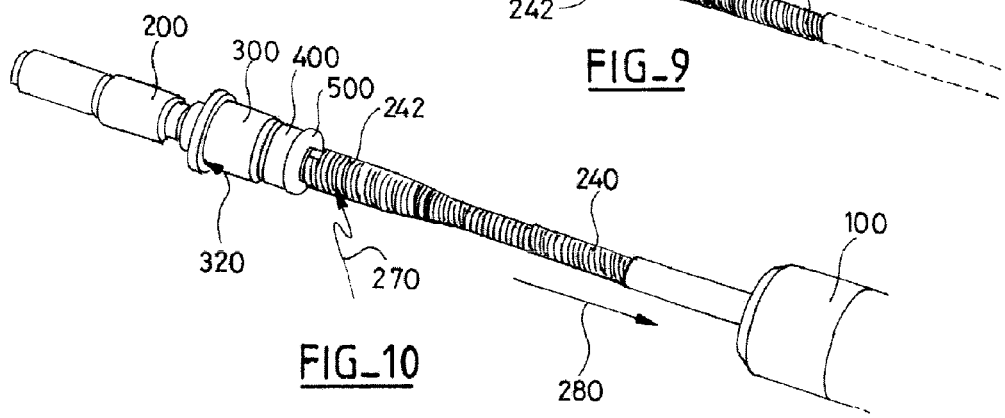
FIG_10
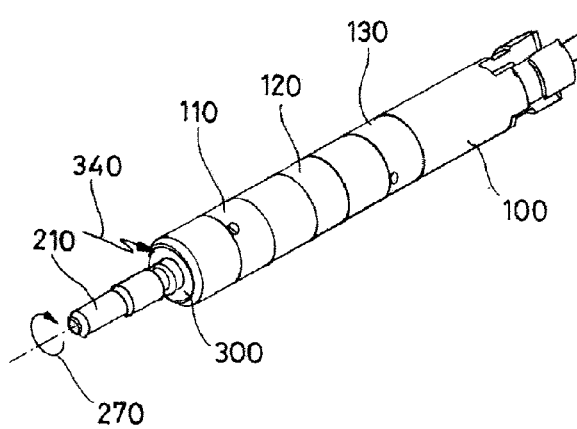
FIG_11

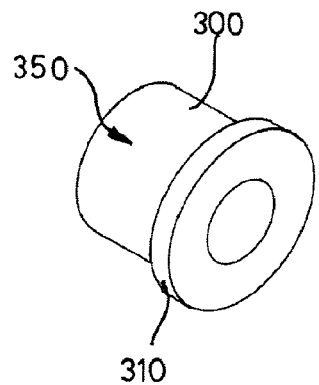
FIG_12a
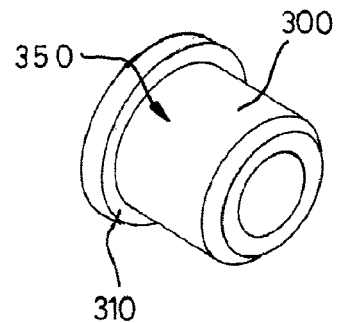
FIG_12b
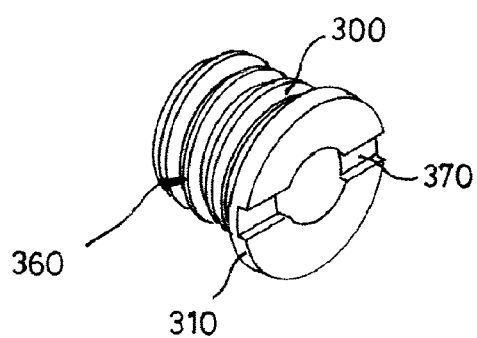
FIG_13a
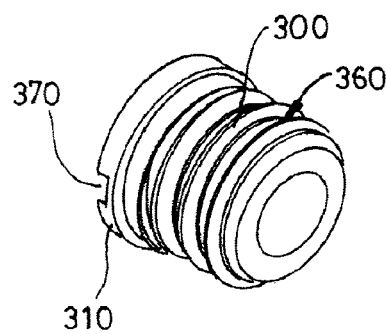
FIG_13b
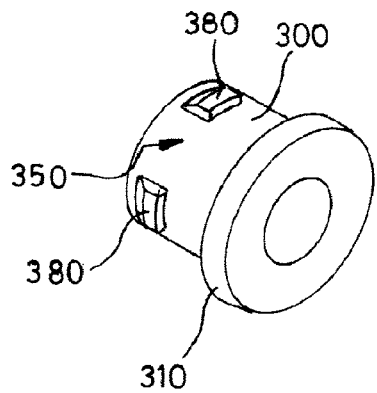
FIG_14a
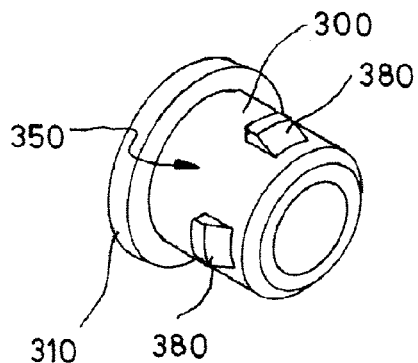
FIG_14b

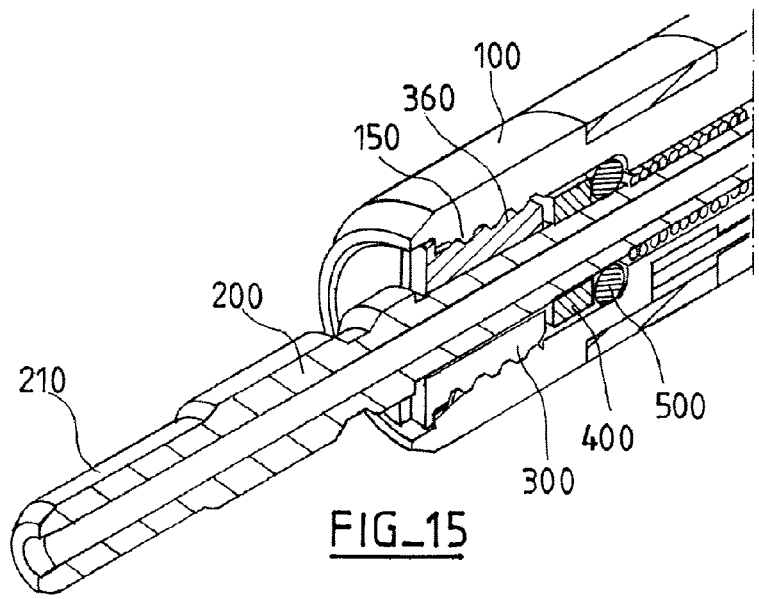
FIG_15
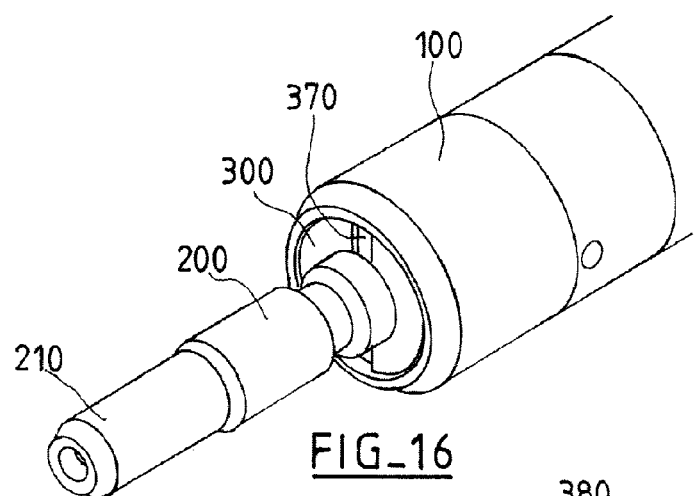
FIG_16
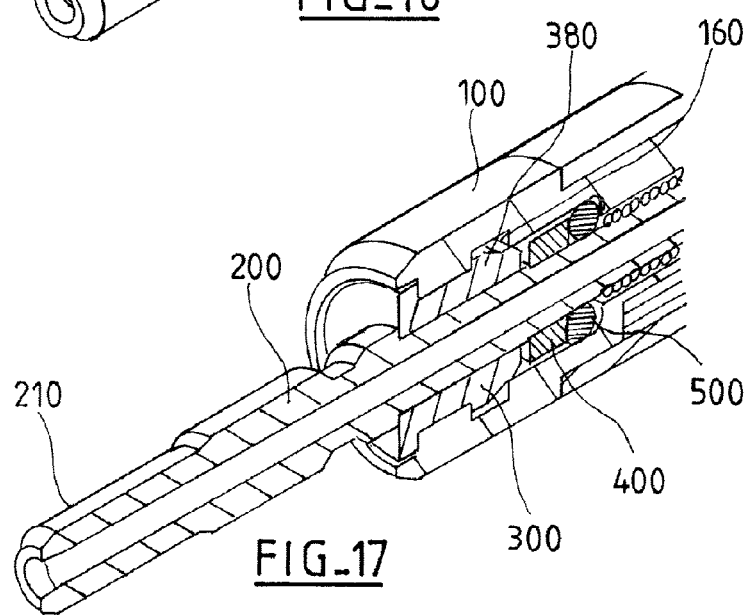
FIG_17

ELECTRICAL CONNECTION PLUG FOR MULTIPOLAR LEAD OF ACTIVE IMPLANTABLE MEDICAL DEVICE

CROSS-REFERENCE TO RELATED PATENT APPLICATIONS

The present application claims the benefit of and priority to France Priority Application No. 1253103, filed Apr. 4, 2012, under 35 U.S.C. §119. The entirety of France Priority Application No. 1253103 is incorporated by reference herein.

FIELD OF THE INVENTION

The present invention relates generally to the field of active implantable medical devices as defined by Directive 90/385/EEC issued Jun. 20, 1990, by the Council of European Communities.

This field includes implants that continuously monitor the cardiac rhythm and, if necessary, deliver to the heart electrical pulses of stimulation, cardiac resynchronization, cardioversion and/or defibrillation. This field also includes neurological devices, cochlear implants, drug diffusion pumps, implantable biological sensors, and the like.

BACKGROUND

Active implantable devices generally include a housing commonly referred to as the generator. The generator is typically electrically and mechanically connected to one or more intracorporeal "leads." These intracorporeal leads are electrodes which are intended contact the bodily tissues (e.g., myocardium tissue, nerve tissue, muscle tissue, etc.) to which electrical stimulation pulses are applied and/or from which an electrical signal is collected.

Standardized connection systems exist to ensure interchangeability of the leads and generators produced by different manufacturers. For example, "IS-1" and "IS-4" standards define a number of dimensional and electrical characteristics relating to pacing or resynchronization pulse delivery leads. For defibrillation leads, wherein the electrical stresses are most severe in view of the high energy to be channeled from the generator to the lead, the "DF-1" and "DF-4" standards define dimensional and electrical characteristics of the connection system.

The present invention more particularly relates to a multipolar electrical connection plug for a lead for an active implantable medical device. A multipolar electrical connection plug is a single-body lead including both stimulation and shock electrodes. The complexity of these leads, which is high due to specific constraints in terms of power related to one or the other uses (i.e., stimulation or shock), is further enhanced by the development of multisite devices and intracardiac sensors such as endocardial acceleration (EA) sensors.

Some leads have a single plug and a plurality of electrical contacts. The plurality of electrical contacts simultaneously connect to various terminals of the generator (e.g. for various energy levels). For example, each of the plurality of electrical contacts may connect to a different generator terminal for the collection of depolarization signals, for the application of pacing pulses, for the delivery of a defibrillation shock energy, or for the transmission of signals collected by a sensor. An advantage of leads having a single plug is that single-plug leads can be subject to single standard. In this context, a single "multipolar" and "isodiameter" connector (e.g., having multiple contacts and a smooth cylindrical shape) to be inserted in a counterpart cylindrical cavity of the connector head of the generator is in compliance with the IS-4/DF-4 standard (ISO 27186-2010).

European Patent Application No. 1641084 A1 and its U.S. counterpart U.S. Patent Application Publication No. 2006/0068645 describe an example of such a four-pole connection plug. Connection plugs of those applications are of the iso-diameter type having an axial electrical contact pin at one end. Connection plugs of those applications also have three annular electrical contact areas on the body of the plug. The annular electrical contact areas are made by consecutive cylindrical rings and are alternately separated by intercalary insulating cylindrical areas. The insulating cylindrical areas electrically isolate the electrical contact areas from one another. Accordingly, it is possible to simultaneously perform all the necessary electrical connections between the generator and the lead pins in a single movement by inserting the connection plug into the cavity of the connector head of the generator.

However, the realization of such a connection plug raises many manufacturing problems and challenges. ISO standards constrain the outer diameter to merely 3.2 mm (e.g., according to ISO 27186), thereby limiting design possibilities. The impact of compliance with such tight dimensional tolerances in an industrial manufacturing process can be significant in terms of time and cost.

A further difficulty arises with respect to "coaxial configuration" leads. Coaxial configuration leads include a mobile central conductor housed in an axial lumen of the lead body and a plurality of other conductors extending from a periphery of the lead body. The axial contact pin is connected to the central conductor. The pin-conductor assembly has a rotational degree of freedom relative to the outer body of the plug and relative to the lead body.

Coaxial configuration leads are mainly used to allow an anchoring screw deployment mechanism (e.g., located at a distal end of the lead) to be driven by manipulation of the proximal end of the lead (e.g., wherein the plug is). For example, a surgeon may hold the proximal end of the lead body with its plug connection with one hand and rotate the pin extending from the plug with the other hand. The torque applied to the pin is transmitted via the inner conductor to the deployment and driving mechanism of the anchoring screw, which allows control of the penetration of the latter into the heart wall. Such a pin-driven lead structure is described, for example, in U.S. Pat. No. 7,241,180 B1 and U.S. Patent Application Publication No. 2010/0211144 A1.

The presence of a movable element in the plug of coaxial configuration leads causes additional difficulties in the design and manufacturing thereof. One difficulty in the design of coaxial configuration leads is attributable to the need to maintain specific dimensional tolerances (e.g., specified by ISO standards) while achieving a minimum functional space necessary for free rotation of the axial pin. Another difficulty is attributable to sealing requirements. In some cases it is advantageous to provide sealing between the external environment and the internal regions of the plug and of the lead body (e.g., including the central lumen which receives the mobile axial conductor). Such sealing functions to prevent the penetration of body fluids between the mobile parts and in the inner areas of the plug and of the lead body. Sealing can be important in the case of a lead with defibrillation electrodes, given the important electrical energy and the high voltage passing through the plug during the application of the defibrillation shock. The structure of such a plug and the method of assembly of the mobile axial pin are challenging and difficult aspects of both the plug design and the implementation of the manufacturing method.

U.S. Patent Application Publication No. 2010/0211144 A1 discloses a pin mounting assembly having two concentric members. The disclosed assembly has a ring-shaped part mounted around the shaft of the pin (e.g., acting as a bearing if the pin is mobile in rotation) and a circumferential collar surrounding the ring around its periphery. The circumferential collar acts as a coupler with the plug body and is encapsulated or screwed during manufacturing. This configuration allows a rotational degree of freedom between the pin and the plug body if necessary. However, the pin mounting assembly disclosed in Publication No. 2010/0211144 leads to a relatively complex and expensive manufacturing process, requiring the production of parts with very tight tolerances in order to meet the imposed dimensional constraints. More importantly, the disclosed configuration fails to provide a satisfactory solution to the issue of very narrow tolerances despite the presence of mobile parts (e.g., the pin possibly being handled without axial or radial clearance with respect to the lead body). Additionally, the disclosed configuration fails to adequately provide absolute tightness of the internal regions of the plug and of the lead body with respect to the external environment.

SUMMARY

The present invention provides solutions to the problems described above by providing new plug configurations. The plug configurations of the present invention can be made by a manufacturing method having relatively few steps, thereby reducing manufacturing costs, while respecting constraints of dimensional tolerances and sealing.

Industrial implementation of the plug according to the present invention is facilitated by the use of parts having basic shapes. Such parts are consequently easy and inexpensive to machine. Industrial implementations of the plugs according to the present invention are further facilitated by reducing the number of parts to be assembled.

The particular configurations of the plugs described herein provide an improved protection of the connection between the central pin and the inner conductor to which the central pin is welded. The described configurations protect the connection against various stresses and reduces the risk of rupture by material fatigue at the pin-conductor interface.

Moreover, although the invention is particularly advantageous in the context of a pin-driven type lead with mobile axial pin, it should be noted that embodiments can also be applied to fixed axial pin leads, given the benefits mentioned above, including ease of industrial implementation.

One implementation of the present disclosure is an electrical connection plug for a multipolar lead of an active implantable medical device (e.g., of a type as disclosed by U.S. Pat. No. 7,241,180 B1 above). That is, a plug having a cylindrical outer surface with a plurality of axially distributed annular contacts and an axial contact at its free end.

In some embodiments, the plug includes an axial pin forming said axial contact at its free end. The end of the axial pin may be made of a conductive material. The plug may further include a mounting pin at its opposite end for connecting to an internal central conductor of the lead. In some embodiments, the plug includes a plug body having a central bore which accommodates the central conductor and the pin rod. The plug body may be made of an insulating material. In some embodiments, the plug body carries the annular contacts at its outer surface and houses the connection conductors to the respective annular contacts.

In some embodiments, the plug further comprises a means of connecting the pin to the plug body. The connecting means may form a connection interface between the pin rod and the inner wall of the bore of the plug body in the vicinity of its outlet. The connection means of the pin to the plug body may include a holding sleeve mounted on the pin rod. An end face of the sleeve may axially abut against a flange formed on the rod. An outer surface of the sleeve may directly radially contact the inner wall of the bore of the plug body at the outlet thereof. The sleeve may be made of a biocompatible polymer material.

In some embodiments, the connection means of the pin to the plug body further includes a locking ring. The locking ring may be secured to the pin rod such that the retaining sleeve is axially clamped between the rod collar and the locking ring. In some embodiments, such clamping leaves a rotational degree of freedom between the sleeve and the pin. The connection means of the pin to the plug body may further include a means for directly securing the sleeve to the plug body at the location of its contact with the inner wall of the bore.

In some embodiments, the means for directly securing the sleeve to the plug body comprises a snap connection with teeth cooperating with an homologous groove. In some embodiments, the snap connection which can be welded or glued.

In some embodiments, the plug further comprises a seal mounted on the pin rod. The seal may be axially clamped between the locking ring and a shoulder of the central bore of the plug body.

One embodiment relates to an electrical connection plug for multipolar lead of an active implantable medical device, said plug having a cylindrical outer surface having a plurality of axially distributed annular contacts (110, 120, 130), and carrying at its free end an axial contact (210), this plug comprising:

An axial pin end (200) of conductive material, forming at its free end said axial contact (210) and having at its opposite end a mounting rod (230) adapted to be connected to an inner central conductor (240) of the lead;

A plug body (140) of insulating material, comprising a central bore (142) housing the central conductor and the pin rod and carrying at its outer surface the annular contacts (110, 120, 130), the plug body also housing of the connection conductors (112, 122, 132) to the respective annular contacts, and Means of connection of the pin to the plug body, forming a connection interface between the pin rod and the inner wall of the bore of the plug body in the vicinity of its outlet, wherein the connection means of the pin to the plug body comprises:

(I) A retaining sleeve (300) mounted on the pin rod (230) so that: (a) axially, the end face (310) of this sleeve abuts against a collar (260) formed on the rod, and (b) radially, the outer surface of the sleeve comes into direct contact with the inner wall of the bore of the plug body (140) at the outlet thereof;

(II) A locking ring (400), secured to the pin rod (230) so that, axially, the retaining sleeve (300) is clamped between the collar of the rod and the locking ring, if necessary leaving a degree of freedom in rotation between the plug and the pin, and (III) Means for directly securing the sleeve (300) to the plug body (140) at the point of its contact with the inner wall of the bore, wherein the direct securing means of the sleeve to the plug body comprises a snap-in connection with notches (380) cooperating with a counterpart groove (160).

BRIEF DESCRIPTION OF THE DRAWINGS

Further features, characteristics and advantages of the present invention will become apparent to a person of ordinary skill in the art from the following detailed description of preferred embodiments. The present invention is described with reference to the following drawings made in which like reference characters refer to like elements and in which:

FIG. 2 is a perspective view in section through an axial plane of the same plug, with its various components assembled, according to an exemplary embodiment.

FIG. 3 shows, separately, in perspective and in axial section, the center pin of the plug shown in FIG. 2 with its retaining sleeve and locking ring, according to an exemplary embodiment.

FIGS. 4 and 5 show perspective views of the annular contacts and the connections formed between such contacts and their respective conductors, according to an exemplary embodiment.

FIG. 6 is a perspective view of the plug body obtained after overmolding the annular contacts of FIG. 5, according to an exemplary embodiment.

FIG. 7 is a perspective view and an axial plan view of the plug body shown in FIG. 6, according to an exemplary embodiment.

FIGS. 8, 9 and 10 show three successive steps of the assembly method of the set associated with the axial pin and its the connection conductor, and of introduction of this assembly into the overmolded plug body of FIG. 6, according to an exemplary embodiment.

FIG. 11 shows the final state of the plug obtained after execution of the various steps of methods of FIGS. 4 to 10, according to an exemplary embodiment.

FIGS. 12*a* and 12*b* illustrate a first exemplary embodiment of the retaining sleeve of the plug of the invention.

FIGS. 13*a* and 13*b* illustrate a second exemplary embodiment of the retaining sleeve of the plug of the invention.

FIGS. 14*a* and 14*b* illustrate a third exemplary embodiment of the retaining sleeve of the plug of the invention.

FIG. 15 is an enlarged, perspective and section view through an axial plane of the end of the plug incorporating a retaining sleeve according to the second embodiment shown in FIGS. 13*a* and 13*b*, according to an exemplary embodiment.

FIG. 16 is an enlarged perspective view, of the plug end of FIG. 15, according to an exemplary embodiment.

FIG. 17 is an enlarged view in perspective and in section through an axial plane, of the end of the plug incorporating a retaining sleeve according to the third embodiment shown in FIGS. 14*a* and 14*b*, according to an exemplary embodiment.

DETAILED DESCRIPTION

Figure 1:
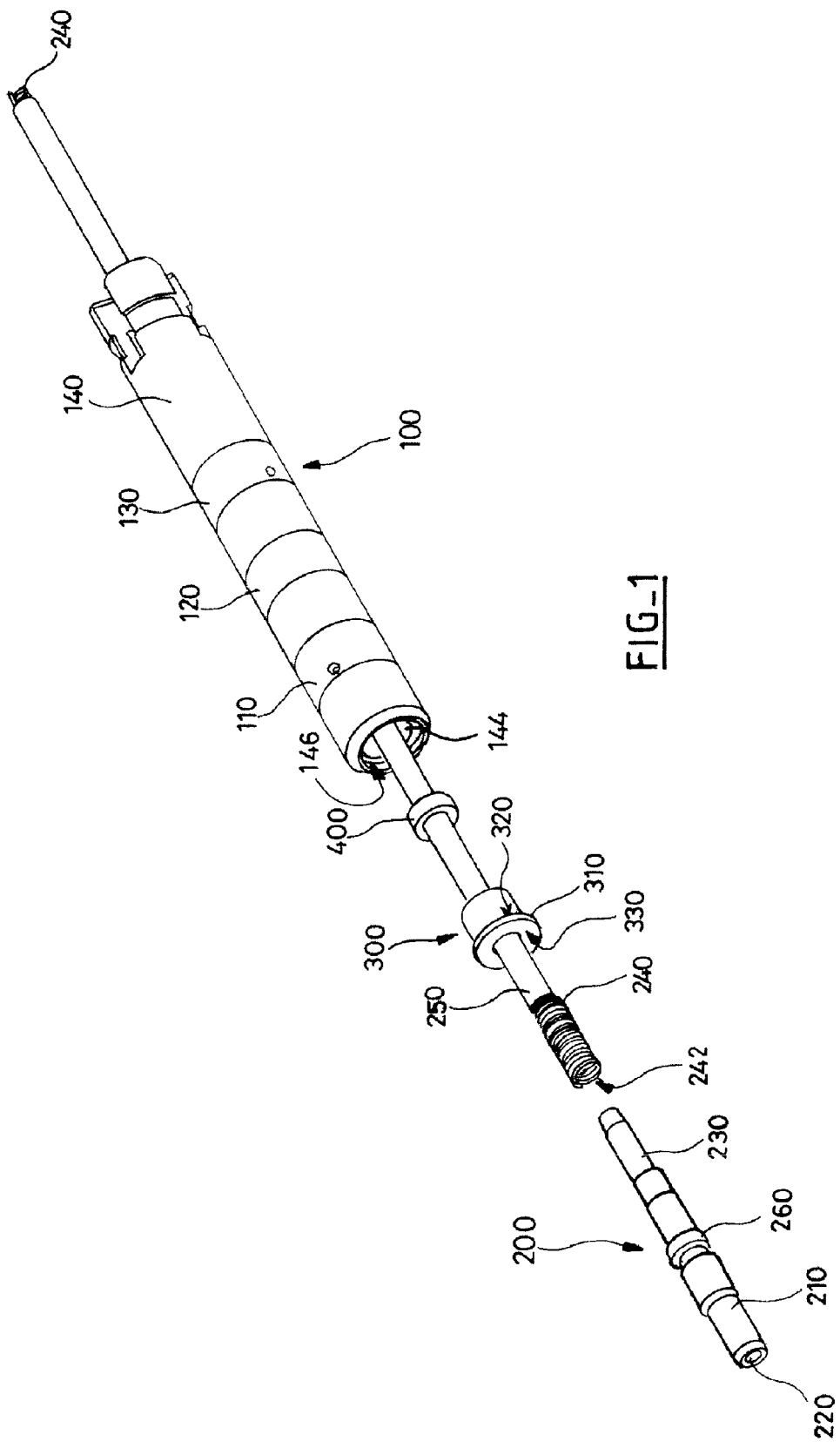
FIG. 1 is an exploded perspective view of a connection plug showing the various components thereof, according to an exemplary embodiment.

Referring to FIGS. 1, 2 and 11, a proximal end of an "isodiameter" multipolar lead is shown. The illustrated isodiameter mulitpolar lead is an example of a lead compliant to the IS-4/DF-4 standard (i.e., ISO 27186). The tip of the lead is a plug to be inserted into a connector head of an implantable generator (e.g. a pacemaker, a defibrillator, a resynchronizer, etc.). FIG. 1 is an exploded view of this plug showing various elements thereof. In FIG. 11, the plug is shown in assembled form, as it appears at the end of the manufacturing process. FIG. 2 shows in more detail the internal structure of this same plug with the configuration of the different parts in their final assembled state.

The illustrated plug is shown to include a plug body 100 having a plurality of annular contacts 110, 120, and 130. The remainder of the plug body may be formed by a piece of insulating material 140. The assembly is shown having an "isodiameter" type. In other words, the assembly is in the form of a smooth cylindrical body. Plug body 100 is shown carrying at its proximal side (i.e., the left side in the figures) an axial pin 200. Pin 200 has an end made of an electrically conductive material. Pin 200 has a free end emerging from a proximal side of the plug body 100 and having an axial contact 210.

The plug is shown as a quadripolar plug (e.g., having three annular contacts and one axial contact). This configuration includes the functionality of a bipolar lead to collect depolarization waves and to apply stimulation pulses between the axial electrode 210 and the ring electrode 110 (e.g., according to the standard IS-4). Additionally, this configuration may be used to apply a defibrillation shock between the two ring electrodes 120 and 130 (e.g., according to the standard DF-4). Alternatively, the electrodes 120 and/or 130, or other additional ring electrodes may be used for connecting to a supply line and/or for the control of circuits incorporated in the lead (e.g., to a sensor located at the end of lead, an endocardial acceleration sensor, etc.). The configuration shown is of course not exhaustive and the invention is applicable to a plug with any number of annular contacts.

Pin 200 is shown to include lumen 220 at the center of pin 200. Lumen 220 may be used for introducing a stylet (i.e. slender probe). A surgeon may use the stylet to guide the lead at the time of implantation into a patient.

Pin 200 is shown to further include a cylindrical mounting rod 230. Mounting rod 230 may be located at the opposite end of the axial contact 210 (e.g., the part located inside the plug body when the plug is assembled). An end of cylindrical mounting rod 230 (e.g., the distal side end, right in the figure) is designed to connect (e.g., physically and electrically) with an internal central conductor 240. The distal end of cylindrical mounting rod 230 may connect to the proximal end 242 of central conductor 240. Conductor 240 may be accommodated in a central bore 142 (as shown in FIG. 2) of plug body 100. Conductor 240 may optionally be free to rotate within central bore 142. In some embodiments, conductor 240 is coated along its length with a sleeve 250 of material having a low friction coefficient (e.g., PTFE). Central bore 142 opens proximally at end 144.

Pin 200 may be a unitary member made of a conductive material (e.g., stainless steel MP35N). Insulating portion 140 of plug body 100 may be made of a biocompatible polymer. In some embodiments, insulating portion 140 may be made of, an insulating material such as polyetheretherketone (PEEK) or a thermoplastic aromatic polyurethane such as tecothane. Such materials are thermoplastic materials which can be easily overmolded with the annular contacts 110, 120, and 130. Such thermoplastic materials can also be easily overmolded with the connection conductors to these rings (e.g., conductor 132 visible in FIG. 2). Contacts 110, 120, and 130 may be made of stainless steel (e.g., stainless steel MP35N).

The connection between pin 200 and plug body 100 may be formed by an assembly including a retaining sleeve 300. Sleeve 300 may be clamped between a flange 260 on the proximal side and a locking ring 400 on the distal side. Flange 260 may be formed on pin 200 between free end 210 and mounting rod 230. These elements are shown separately in FIG. 3, mounted on pin 200.

This configuration provides substantially zero axial space between sleeve 300 and the assembly formed of the pin 200 and ring 400. In some embodiments, ring 400 may be secured to pin 200 so as to constitute a rigid assembly therewith. This configuration provides a degree of freedom in rotation between pin 200 and sleeve 300 (which may be advantageous for a pin-driven type lead). The possibility of rotation is shown by arrow 270. In some embodiments, sleeve 300 has a shoulder 310 on the proximal side thereof. Shoulder 310 defines a face 320 on the distal side thereof. Face 320 may be sized, shaped, and/or oriented to come into contact with a counterpart shoulder 146 located at the outlet of the inner lumen 144 of the plug body. Shoulder 310 also defines a face 330 on the proximal side thereof. Face 330 may come into direct contact with collar 260 of pin 200.

Sleeve 300 is directly secured to plug body 100 at the point of its contact with the inner wall of the inner bore. This allows a very simple mounting, thereby ensuring compliance with dimensional tolerances. Sleeve 300 can form a seal with the central bore 142 of the plug body 100. With respect to the seal, it is also possible to provide a ring seal 500 (e.g., as shown in FIG. 2). Ring seal 500 may be made, for example, of silicone compressed between the distal face of the ring 400 and a shoulder 148 via central bore 142 of plug body 100. Ring seal 500 may be provided in the case of a pin-driven type lead.

Ring 400 may be made of a material that can be easily secured to plug assembly 230 of pin 200. For example, ring 400 may be made of stainless steel MP35N. Support sleeve 300 may be made of a material that can be easily secured to the insulating portion 140 of the plug body. For example, sleeve 300 may be made of PEEK or Tecothane.

Referring now to FIGS. 4 to 11, a process for manufacturing the described plug is shown, according to an exemplary embodiment. The first step in the manufacturing process is the realization of the plug body 100, overmolded with its annular contacts 110, 120, 130. The annular contacts may be prepared separately (as shown in FIG. 4). The annular contacts may be prepared, for example, by welding a terminal 114 to the inside of a contact 110. Terminal 114 may also be welded or crimped to a corresponding conductor 112. In some embodiments, contact 110 and terminal 114 may be two components of a single unitary piece.

As shown in FIG. 5, the various annular contacts 110, 120, 130 provided with their respective conductors 112, 122, 132 are then positioned relative to each other based on the configuration that they will have on the plug body in its final state. The insulating portion 140 of the plug body (e.g., made of biocompatible polymer) may then be overmolded with the contacts 110, 120, 130 as shown in FIG. 6, leaving a central lumen 142.

Referring to FIG. 6 and FIG. 7, the sub-assembly thus obtained is shown in section view. Note in particular that at the outlet 144 of central bore 142, there is no overmolded part or insert. Rather, only the outlet 144 with the shoulder 146 is provided to further receive the support sleeve. In other words, the part obtained at this stage of the method is a part made entirely of insulating material, with the exception of the annular contacts and of their connection conductors.

Referring to FIGS. 8, 9, and 10, the pin and the parts serving to form the connection interface are assembled as shown. The pin and parts shown in FIGS. 8, 9, and 10 may be assembled separately from the sub-assembly shown in FIGS. 6 and 7. The first step in assembling the connection interface (shown in FIG. 8) is to place the support sleeve 300 on mounting rod 230 of pin 200. When sleeve 300 is placed on rod 230, face 330 of this sleeve abuts against collar 260. Locking ring 400 is then also threaded on mounting rod 230 so as to press ring 300 against collar 260. Then ring 400 is secured to pin 200 in the position shown in FIG. 9. Ring 400 may be secured to bin 200 by laser welding 410, gluing, screwing, crimping, or other suitable fastening means.

Referring specifically to FIG. 9, an optional seal 500 may be placed around mounting rod 230 and against ring 400. After placing seal 500, the next step is to weld end 242 of axial conductor 240 on the end of mounting rod 230 (e.g., using laser welding 270 as shown in FIG. 10). The sub-assembly thus obtained is shown in FIG. 10 in its final state.

Referring specifically to FIG. 10, the next step is to introduce (e.g., shown by arrow 280) this sub-assembly within the inner lumen of plug body 100. The sub-assembly may be introduced to plug body 100 from the proximal end of plug body 100 until face 320 of support sleeve 300 proximally abuts against the plastic material of body 140. These two elements are then joined together using, for example laser welding 340 as shown in FIG. 11, gluing, ultrasonic welding, chemical welding or another suitable method.

In some embodiments, axial conductor 240 is prepared concurrently with plug body 100 and combines with plug body 100 to form an assembly. Axial conductor 240 may then be mounted on another assembly (e.g., shown in FIG. 8), thereby including pin 200, retaining sleeve 300, and locking ring 400, as assembled together. In some embodiments seal 500 may be inserted onto the rod of the pin prior to welding. Axial conductor 240 may be welded to mounting rod 230, resulting in the configuration illustrated in FIG. 10.

Referring now to FIG. 11, the final state of the plug obtained after execution of the various method steps of FIGS. 4 to 10 is shown, according to an exemplary embodiment. It is emphasized that the connection of the two subassemblies (e.g., the plug body resulting from steps of FIGS. 5 to 7 and the pin provided with the various associated elements resulting from steps of FIGS. 8 and 9) is direct without intermediary components. Note in particular that sleeve 300 and polymer 140 of the plug body may be made of identical or similar materials (e.g., two biocompatible polymers). This material selection may facilitate joining and securing the two subassemblies while guaranteeing compliance with dimensional tolerances and sealing requirements without requiring the implementation of complex manufacturing techniques. These requirements may be met even in a configuration of the pin-driven type with one degree of freedom in rotation between pin end 210 and plug body 100. For example, these requirements are met even in a configuration in which rotation 270 imparted to axial pin 210 is transmitted (as shown at 290 in FIG. 11) over the entire length of the central conductor 240.

Referring now to FIGS. 12-17, various exemplary embodiments of retaining sleeve 300 are illustrated. FIGS. 12a and 12b correspond to a first embodiment, which is illustrated in FIGS. 1-11 as described above. The first embodiment is shown to include a smooth outer surface 350 inserted into a recess (in conjugated form) located at the outlet of the plug body. Ring 310 may be glued or welded to the plug body.

Referring now to FIGS. 13a and 13b, a second embodiment of retaining sleeve 300 is shown. The second embodiment is shown in assembled form in FIGS. 15 and 16. In the second embodiment, the outer surface of sleeve 300 is provided with a thread 360. Thread 360 may engage a homologous thread 150 formed in plug body 100 (as shown in FIG. 15). On the apparent front face, a footprint 370 (e.g., a slot, notch, indentation, etc.) may be provided for an appropriate tool to achieve screwing of sleeve 300 in the plug body (see also FIG. 16). In some embodiments, sleeve 300 and plug body 100 may be glued or welded together can be done in addition to securing via threads 360 and 150.

Referring to FIGS. 14a and 14b, a third embodiment of retaining sleeve 300 is shown. The third embodiment is characteristic of the invention illustrated in FIGS. 14a, 14b and 17. In the third embodiment, an outer surface 350 of sleeve 300 is provided with notches 380. Notches 380 may cooperate with a counterpart groove 160 (as shown in FIG. 17) formed in the plug body. This cooperation allows placement of sleeve 300 by direct snapping into the plug body. In some embodiments, gluing or welding of these two elements may be performed to enhance the connection therebetween.

What is claimed is:

1. An electrical connection plug for a multipolar lead of an active implantable medical device, the electrical connection plug comprising:
    an axial pin having a free end forming an axial electrical contact, a mounting rod adapted to connect with an inner central conductor, and a flange extending radially from the axial pin between the free end and the mounting rod;
    a retaining sleeve having a cylindrical bore through which the axial pin is inserted, a first end face of the retaining sleeve abutting the flange extending radially from the axial pin, and a second end face opposite the first end face;
    a locking ring inserted onto the axial pin and fixedly attached to the axial pin such that the locking ring abuts the second end face of the retaining sleeve; and
    wherein the retaining sleeve is secured axially between the radially extending flange and the locking ring, thereby preventing axial movement of the retaining sleeve relative to the axial pin while permitting rotation of the retaining sleeve relative to the axial pin;
    a plug body having a central bore housing the central conductor and the axial pin and carrying at its outer surface a plurality of annular electrical contacts;
    wherein the plug body houses a plurality of connection conductors, each connection conductor electrically connected with a different annular electrical contact;
    wherein the central conductor is coated with a lubricant to reduce rotational friction and facilitate rotation of the central conductor within the central bore.

2. The electrical connection plug of claim 1, wherein the plug body includes a shoulder extending radially inward from a circumferential face of the central bore, the electrical connection plug further comprising:
    a seal inserted onto the axial pin and axially secured between the locking ring and the shoulder,
    wherein the seal is prevented from moving axially along the axial pin.

3. The electrical connection plug of claim 1, wherein the retaining sleeve includes a shoulder extending radially outward from an outer circumferential face thereof, wherein the shoulder defines a radial face adapted to abut a counterpart shoulder located at an outlet of the central bore.

4. The electrical connection plug of claim 1, wherein the plug body is overmolded onto the annular electrical contacts and forms a smooth circumferential surface aligned with outer circumferential surfaces of each of the annular electrical contacts.

5. The electrical connection plug of claim 1, wherein the retaining sleeve is made of a biocompatible polymer material.

6. The electrical connection plug of claim 1, wherein an outer circumferential face of the retaining sleeve directly contacts an inner circumferential face of the central bore.

7. The electrical connection plug of claim 6, further comprising:
    a mechanism for directly securing the outer circumferential face of the retaining sleeve to the inner circumferential face of the central bore.

8. The electrical connection plug of claim 7, wherein the mechanism for directly securing the outer circumferential face of the retaining sleeve to the inner circumferential face of the central bore is a threaded connection between the outer circumferential face of the retaining sleeve to the inner circumferential face of the central bore,
    wherein the outer circumferential face of the retaining sleeve includes threads configured to engage corresponding threads of the inner circumferential face of the central bore.

9. The electrical connection plug of claim 7, wherein the mechanism for directly securing the outer circumferential face of the retaining sleeve to the inner circumferential face of the central bore is a snap connection between the outer circumferential face of the retaining sleeve to the inner circumferential face of the central bore,
    wherein the outer circumferential face of the retaining sleeve includes one or more notches configured to engage a corresponding groove in the inner circumferential face of the central bore.

10. The electrical connection plug of claim 7, wherein the mechanism for directly securing the outer circumferential face of the retaining sleeve to the inner circumferential face of the central bore is an adhesive or weld between the outer circumferential face of the retaining sleeve to the inner circumferential face of the central bore.

11. A process for manufacturing an electrical connection plug for multipolar lead of an active implantable medical device, the method comprising:
    providing an axial pin having a free end forming an axial electrical contact, a mounting rod adapted to connect with an inner central conductor, and a flange extending radially from the axial pin between the free end and the mounting rod;
    inserting the axial pin through a cylindrical bore in a retaining sleeve such that an end face of the retaining sleeve abuts a flange extending radially from the axial pin;
    inserting the axial pin through a locking ring which abuts a second face of the retaining sleeve;
    forming a plug body having a central bore, the central bore defining an inner circumference;
    securing the retaining sleeve to an inner circumference of the plug body such that the retaining sleeve is secured axially to the plug body and the axial pin is allowed to rotate relative to the plug body and the retaining sleeve;
    wherein the inner central conductor is coated with a lubricant to reduce rotational friction and facilitate rotation of the central conductor within the central bore.

12. The process of claim 11, wherein the plug body includes a shoulder extending radially inward from a circumferential face of the central bore, and wherein the process further comprises:
    inserting a seal onto the axial pin such that the seal is axially secured between the locking ring and the shoulder, wherein the seal is prevented from moving axially along the axial pin.

13. The process of claim 11, wherein an outer circumferential face of the retaining sleeve directly contacts an inner circumferential face of the central bore during and after the securing step.

14. The process of claim 13, wherein the mechanism for directly securing the outer circumferential face of the retaining sleeve to the inner circumferential face of the central bore is a threaded connection between the outer circumferential face of the retaining sleeve to the inner circumferential face of the central bore, wherein the outer circumferential face of the retaining sleeve includes threads configured to engage corresponding threads of the inner circumferential face of the central bore.

15. The process of claim 13, wherein the mechanism for directly securing the outer circumferential face of the retaining sleeve to the inner circumferential face of the central bore is a snap connection between the outer circumferential face of the retaining sleeve to the inner circumferential face of the central bore, wherein the outer circumferential face of the retaining sleeve includes one or more notches configured to engage a corresponding groove in the inner circumferential face of the central bore.

16. The process of claim 13, wherein the mechanism for directly securing the outer circumferential face of the retaining sleeve to the inner circumferential face of the central bore is an adhesive or weld between the outer circumferential face of the retaining sleeve to the inner circumferential face of the central bore.

17. An electrical connection plug for multipolar lead of an active implantable medical device, comprising:

a cylindrical outer surface having a plurality of axially distributed annular contacts, and carrying at one free end an axial contact;

an axial pin end of conductive material comprising an axial contact at one end and a mounting rod at a second end, the mounting rod connected to an inner central conductor of the lead;

a plug body of insulating material, comprising a central bore housing the central conductor and the pin rod and carrying at its outer surface the annular contacts, the plug body also housing of the connection conductors to the respective annular contacts, and a connection device between the pin and the plug body, forming a connection interface between the pin rod and the inner wall of the bore of the plug body in the vicinity of its outlet, wherein the connection device of the pin to the plug body comprises:

(a) a retaining sleeve mounted on the pin rod so that: axially, the end face of this sleeve abuts against a collar formed on the rod, and radially, the outer surface of the sleeve comes into direct contact with the inner wall of the bore of the plug body at the outlet thereof;

(b) a locking ring, secured to the pin rod so that, axially, the retaining sleeve is clamped between the collar of the rod and the locking ring, if necessary leaving a degree of freedom in rotation between the plug and the pin, and (c) means for directly securing the sleeve to the plug body at the point of its contact with the inner wall of the bore;

wherein the central conductor is coated with a lubricant to reduce rotational friction and facilitate rotation of the central conductor within the central bore.

* * * * *